(12) United States Patent
Kirchberg et al.

(10) Patent No.: US 11,107,270 B2
(45) Date of Patent: Aug. 31, 2021

(54) MEDICAL SCENE MODEL

(71) Applicant: Siemens Healthcare GmbH, Erlangen (DE)

(72) Inventors: Klaus J. Kirchberg, Plainsboro, NJ (US); Vivek Kumar Singh, Princeton, NJ (US); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 42 days.

(21) Appl. No.: 16/183,238

(22) Filed: Nov. 7, 2018

(65) Prior Publication Data
US 2019/0139300 A1 May 9, 2019

(30) Foreign Application Priority Data

Nov. 8, 2017 (EP) .................................... 17200642

(51) Int. Cl.
*G06T 17/00* (2006.01)
*G01B 11/22* (2006.01)
(Continued)

(52) U.S. Cl.
CPC ............ *G06T 17/00* (2013.01); *G01B 11/026* (2013.01); *G01B 11/22* (2013.01); *G01B 11/2513* (2013.01); *G01B 11/2545* (2013.01); *G01S 17/89* (2013.01); *G06K 9/00771* (2013.01); *G06T 15/00* (2013.01); *G06T 19/20* (2013.01); *G16H 30/40* (2018.01); *G16H 40/20* (2018.01); *G16H 40/63* (2018.01); *A61B 5/0037* (2013.01); *A61B 5/0077* (2013.01); *A61B 5/021* (2013.01);
(Continued)

(58) Field of Classification Search
None
See application file for complete search history.

(56) References Cited

U.S. PATENT DOCUMENTS

| 2015/0009214 A1* | 1/2015 | Lee .......................... G06T 17/10 345/420 |
| 2015/0213646 A1 | 7/2015 | Ma et al. |

(Continued)

FOREIGN PATENT DOCUMENTS

WO  WO2012137116 A1  10/2012

OTHER PUBLICATIONS

Anguelov, Dragomir, et al. "SCAPE: shape completion and animation of people." ACM transactions on graphics (TOG). vol. 24. No. 3. ACM, 2005. p. 1-9.
(Continued)

*Primary Examiner* — Yi Wang
(74) *Attorney, Agent, or Firm* — Lempia Summerfield Katz LLC

(57) ABSTRACT

A method of deriving one or more medical scene model characteristics for use by one or more software applications is disclosed. The method includes receiving one or more sensor data streams. Each sensor data stream of the one or more sensor data steams includes position information relating to a medical scene. A medical scene model including a three-dimensional representation of a state of the medical scene is dynamically updated based on the one or more sensor data streams. Based on the medical scene model, the one or more medical scene model characteristics are derived.

19 Claims, 4 Drawing Sheets

(51) Int. Cl.

| | |
|---|---|
| *G01B 11/25* | (2006.01) |
| *G06T 19/20* | (2011.01) |
| *G16H 40/63* | (2018.01) |
| *G06K 9/00* | (2006.01) |
| *G16H 30/40* | (2018.01) |
| *G01B 11/02* | (2006.01) |
| *G06T 15/00* | (2011.01) |
| *G01S 17/89* | (2020.01) |
| *G16H 40/20* | (2018.01) |
| *G16H 30/20* | (2018.01) |
| *A61B 5/00* | (2006.01) |
| *A61B 5/055* | (2006.01) |
| *A61B 5/021* | (2006.01) |
| *A61B 5/318* | (2021.01) |

(52) U.S. Cl.
CPC ............... *A61B 5/055* (2013.01); *A61B 5/318* (2021.01); *A61B 5/4887* (2013.01); *A61B 5/744* (2013.01); *G06K 9/00201* (2013.01); *G06T 2210/36* (2013.01); *G06T 2210/41* (2013.01); *G06T 2219/2004* (2013.01); *G16H 30/20* (2018.01)

(56) References Cited

U.S. PATENT DOCUMENTS

| | | | |
|---|---|---|---|
| 2015/0269258 A1* | 9/2015 | Hunt, Jr. | G06F 16/955 707/770 |
| 2015/0356782 A1 | 12/2015 | Miller et al. | |
| 2016/0005229 A1* | 1/2016 | Lee | G06F 3/0488 345/419 |
| 2016/0093078 A1* | 3/2016 | Davis | G06F 16/58 345/629 |
| 2017/0091939 A1 | 3/2017 | Kluckner et al. | |
| 2017/0091940 A1 | 3/2017 | Ma et al. | |
| 2018/0101966 A1* | 4/2018 | Lee | H04N 21/44012 |

OTHER PUBLICATIONS

European Office Action for European Patent Application No. 17200642.1-1230 dated May 30, 2018.

Technische Universitäat München et al.: "Dynamic sensor fusion", YouTube, pp. 1-3, XP054978344, Retrieved from the Internet: URL:https://www.youtube.com/watch?v=FidCx6 kiv6c—2010.

* cited by examiner

MEDICAL SCENE MODEL

This application claims the benefit of EP17200642.1, filed on Nov. 8, 2017, which is hereby incorporated by reference in its entirety.

TECHNICAL FIELD

The present embodiments relate to medical scene models.

BACKGROUND

Existing medical workflows may be inefficient. For example, medical imaging and image based interventions, such as medical scanning, may be expensive and time consuming. For example, for known computerized tomography (CT) scanners, a patient lies on a table, and a technician then sets the correct height of the table and aligns the correct portion of the patient for optimal scanning This may include a test scan before a full scan, to provide that the position of an internal portion of the patient relative to the scanner is correct. Parameters are set by the technician, such as a radiation dose judged based on patient size. The overhead associated with patient preparation, positioning, and scan parameter setting by a technician may impair efficient scanner utilization. Medical workflows other than medical imaging may suffer from similar inefficiencies.

From US 2015/0213646 A1, a method and apparatus is known for generating a 3D personalized mesh of a person from a depth camera image for medical imaging scan planning. A static personalized 3D avatar mesh of the subject is generated from a single snapshot from a depth camera sensor. Generating the avatar is subject to constraints that take into account clothing worn by the subject and the presence of a table on which the subject is lying. Dynamics of a medical scenario environment are not taken into account.

It is desirable to improve the efficiency of medical workflows, whilst still maintaining the continuity and reliability that are important in medical environments.

SUMMARY AND DESCRIPTION

According to a first aspect, a method of deriving one or more medical scene model characteristics for use by one or more software applications includes receiving one or more sensor data streams. Each sensor data stream includes position information relating to a medical scene. The method includes dynamically updating, based on the one or more sensor data streams, a medical scene model including a three-dimensional representation of a state of the medical scene, and deriving, based on the medical scene model, the one or more medical scene model characteristics.

One or more of the sensor data streams may include information relating to an image of the medical scene.

One or more of the sensor data streams may include depth information relating to the depth, from a sensor, of one or more objects of the medical scene.

The one or more sensor data streams may be received from a respective plurality of sensors, and the method may include determining a coordinate transformation for transforming a coordinate system for one or more of the sensors into a medical scene model coordinate system. The dynamically updating the medical scene model may be based at least in part on the determined coordinate transformation.

The method may include dynamically adding one or more sensor data streams to, and/or dynamically removing one or more sensor data streams from, the one or more sensor data streams that are received.

The method may include: analyzing the one or more sensor data streams to determine positions of one or more objects of the medical scene in a or the medical scene model coordinate system. The dynamically updating the medical scene model may be based at least in part on the determined positions.

The method may include analyzing the one or more sensor data streams to recognize one or more objects of the medical scene. The method may also include determining, based on the analyzing, a representation for the one or more recognized objects. The dynamically updating the medical scene model may include including the determined representation into the medical scene model.

The determining the representation for the one or more recognized objects may include determining one or more geometric models representing the geometry of the one the one or more recognized objects.

One or more of the objects of the medical scene may be a patient, and the determined representation may include a model of a patient.

The method may include receiving medical imaging data from a medical imaging scanner of the medical scene. The dynamically updating the medical scene model may be based at least in part on the medical imaging data.

The method may include receiving further medical imaging data from a further medical imaging scanner of the medical scene. The dynamically updating the medical scene model may be based at least in part on the further medical imaging data, and the method may further include determining a relative position of the medical imaging scanner and the further medical imaging scanner. The method may include fusing, based on the determined relative position, the medical imaging data with the further medical imaging data.

The method may include determining, based on the one or more data streams and/or based on the medical scene model, one or more accuracy parameters for the one or more medical scene model characteristics. Each accuracy parameter relates to an estimate of the accuracy of the respective medical scene model characteristic.

The method may include streaming the one or more medical scene model characteristics to an interface for use by the one or more software applications.

The method may include analyzing the one or more scene model characteristics to determine one or more control signals for controlling one or more objects of the medical scene, and transmitting the one or more control signals to the one or more objects.

At least one of the one or more sensor data streams may be from a sensor of one of the one or more objects to which the one or more control signals is transmitted.

At least one of the objects of the medical scene may be a medical imaging scanner, and the method may include determining, based on the one or more medical scene characteristics, a position of a patient, determining, based on the position of the patient, an estimate of the position of one or more portions of the patient, and determining, based on the determined estimate of the position of one or more portions of the patient, one or more control signals for controlling the medical imaging scanner.

The method may include determining, based on the one or more medical scene characteristics, a position of a radiation source, and estimating, based on the determined position of the radiation source, a radiation characteristic at one or more locations in the medical scene model.

The method may include receiving information from the software application, and determining, based on the received information, a detail level for the medical scene model. The dynamically updating the medical scene model may be based at least in part on the determined detail level.

The method may include rendering the medical scene model to produce a representation of the medical scene model projected on a two-dimensional plane.

One or more of the sensor data streams may each include a stream of data packets, and each data packet may include a time stamp provided by a sensor clock of the sensor from which the data packet is acquired.

The method may include synchronizing one or more of the sensor clocks with a clock associated with the medical scene model.

The method may include determining one or more dynamic changes to the medical scene model, and storing the determined one or more dynamic changes.

The method may include determining, based on the stored one or more dynamic changes, a trajectory of one or more objects of the scene model.

According to a second aspect, an apparatus for deriving one or more medical scene model characteristics for use by one or more software applications is configured to perform the method according to the first aspect.

According to a third aspect, a computer program includes instructions that, when executed on a computer, cause the computer to perform the method according to the first aspect.

DETAILED DESCRIPTION

Figure 1:
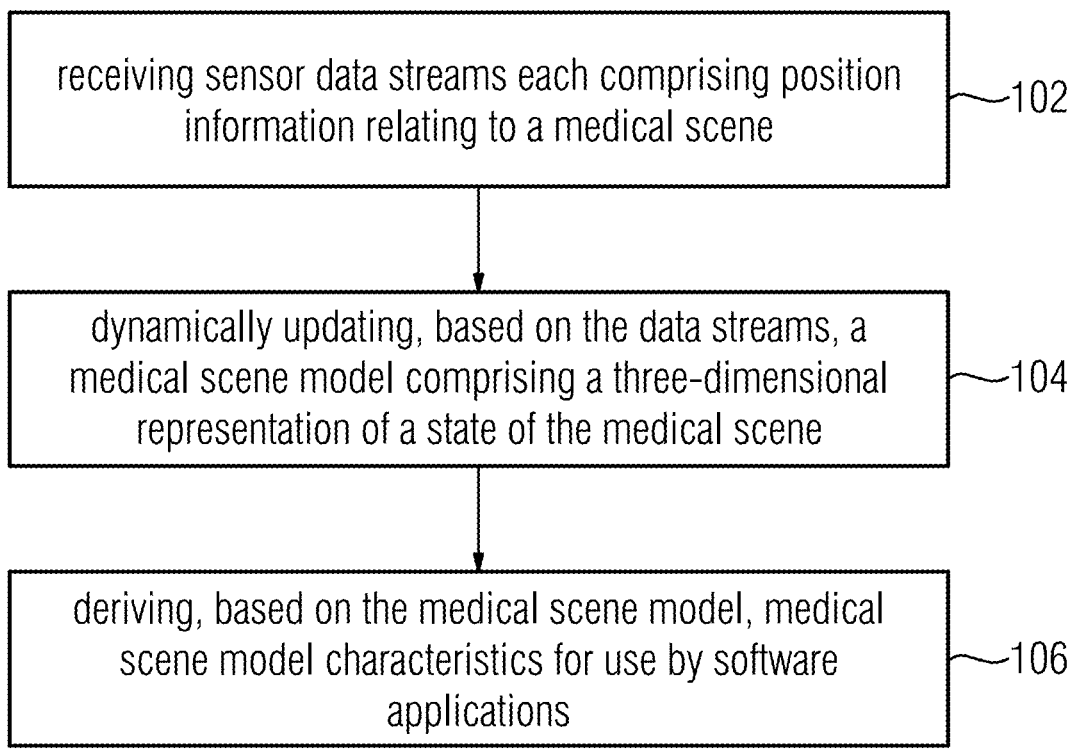
FIG. 1 illustrates schematically an example flow diagram illustrating a method according to an example.

FIG. 1 illustrates schematically acts of a method of deriving one or more medical scene model characteristics for use by one or more software applications, according to an example.

Figure 2:
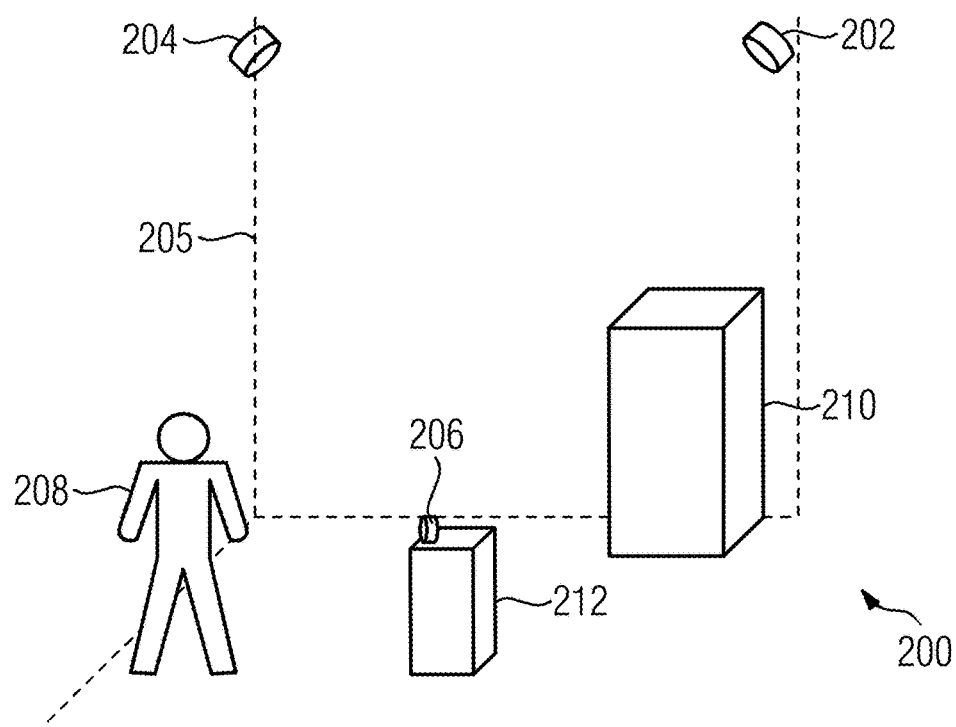
FIG. 2 illustrates schematically a medical scene according to an example.

An example medical scene 200 is illustrated schematically in FIG. 2. The example medical scene 200 of FIG. 2 includes a plurality of objects 208, 212, 210 in a room 205. The objects in this example are a person 208 (e.g., a patient 208), a medical imaging or therapy device 210 (e.g., a CT scanner 210), and a workstation 212. Each of the objects 208, 212, 210 may be moveable. For example, the patient 208 may move according to the patient's will, and the scanner 210 and the workstation 212 may be controllable to move (e.g., to change) the location and/or configuration of the scanner 210 and the workstation 212. The medical scene 200 includes sensors 204, 202, 206. Two sensors 202, 204 are located at upper corners of the room 205 and are positioned to monitor the medical scene 200. In this example, the sensors 202, 204 are installed at fixed locations in the room 205 and cover a common area of interest from different points of view. A further sensor 206 is located on the workstation 212, for example, so as to monitor a position of the workstation 212 or other objects.

Figure 3:
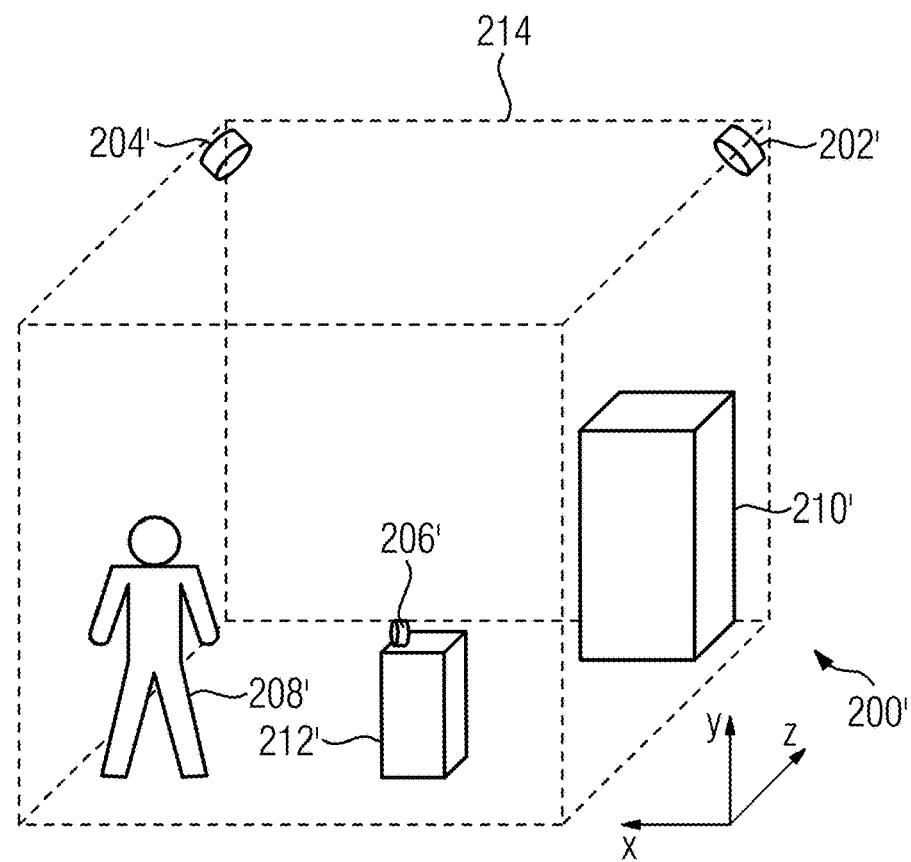
FIG. 3 illustrates schematically a medical scene model of the medical scene of FIG. 2, according to an example.

An example medical scene model 200', including a three-dimensional representation 214 of a state of the medical scene 200, is illustrated schematically in FIG. 3. The representation 214 may be defined within a three-dimensional cartesian coordinate system x, y, z. Components of the medical scene model 200' of FIG. 3 representing the components of the medical scene 200 of FIG. 2 are given the same reference numerals as the component of the medical scene 200 but followed by a prime ('). The representation 214 includes representations 202', 204', 206', 208', 210', 212' of the sensors 202, 204, 206, and objects 208, 201, 212 of the medical scene 200. A medical scene model characteristic includes information characterizing the medical scene model 200'.

Returning to FIG. 1, in act 102, the method includes receiving one or more sensor data streams. Each sensor data stream includes position information relating to the medical scene 200.

For example, the sensor data streams may be received from one or more of the sensors 202, 204, 206 of the medical scene 200.

One or more of the sensor data streams may include information relating to an image of the medical scene. For example, one or more of the sensors 202, 204 positioned to monitor the medical scene 200 may capture successive images of the medical scene 200, and the data stream may include the successive images. For example, the sensors 202, 204 may be RGB (color) cameras, and the images may be, for, example, RGB (color) images. For example, each sensor 202, 204 may include two cameras offset from one another, and the position of one or more of the objects 208, 210, 212 may be determined based on images from the two cameras using stereo triangulation or other techniques.

One or more of the sensor data streams may include depth information relating to the depth, from a sensor 202, 204, of one or more objects 208, 210, 212 of the medical scene 200. For example, the sensors may be RGBD (color and depth) cameras, and the image streams may include color information and depth information. For example, one or more of the sensors 202, 204 may include time-of-flight modules to determine the depth information. For example, the sensors may measure the time taken for light emitted from the sensor to travel to an object and return to the sensor, and calculate the distance of the object from the sensor based on this measured time. As another example, one or more of the sensors 202, 204 may include structured light modules to determine the depth information. For example, light having a known structure at a known distance (e.g., a speckle pattern of a infra-red laser) may be cast by the sensor onto the medical scene 200. An infra-red camera of the sensor 202, 204 may image the medical scene 200 and hence the light structure pattern as the light structure pattern has fallen on the objects 208, 210, 212 of the medical scene 200. The sensor may then determine, from differences between the known light structure at the known distance and the imaged light structure as has been modified by the objects 208, 210, 212, the distance of each object 208, 210, 212 from the sensor 202, 204. As another example, the sensors 202, 204 may be or include other depth sensing devices such as Light Detection and Ranging (LIDAR) devices, that measure the distance to a target by illuminating that target with a pulsed laser light, and then measuring the reflected pulses. The one or more data streams including depth information may provide for the three-dimensional positions of objects 208, 210, 212 within the medical scene 200 to be more accurately and reliably determined.

One or more of the sensor data streams may include information on the location of one or more of the objects 208, 210, 212. For example, the sensor 206 attached to the moveable workstation 212 of the medical scene 200 may be a position sensor 206. For example, the position sensor 206 may be arranged to determine a location of the position sensor 206 in the room 205 relative to one or more reference points, and the sensor data stream may be or include the determined location at successive times. Since the position sensor 206 is attached to the moveable workstation 212, the location of the workstation 212 relative to the one or more reference points may be accordingly determined. A position sensor may be attached to any object 208, 212, 210 of the medical scene 200 (e.g., to tablet computers) or to medical equipment carts and the like.

One or more of the sensor data streams may include information on a configuration of one or more of the objects 210, 212, and hence a position of the object 210, 212 in space. For example, the medical scanner or therapy device 210 may include a robotic arm (not shown) having joints (not shown) connecting arm components (not shown), and the sensor data stream may include information from one or more sensors located at one or more of the joints. The information may include the relative orientation of one arm component to another arm component at one or more of the joints at successive times. The configuration and hence position of the robotic arm in space may be determined, for example, from the orientation information and known lengths of each arm component, for example.

In act 104, the method includes dynamically updating, based on the one or more sensor data streams, the medical scene model 200' including the three-dimensional representation 214 of a state of the medical scene 200.

As described above, the one or more sensor data streams each include position information relating to the medical scene 200. In one example, the medical scene model 200' is or includes a geometric model, and the three-dimensional representation 214 of the state of the medical scene 200 is defined with respect to a medical scene model coordinate system x, y, z. The method may therefore include determining a coordinate transformation for transforming a coordinate system for one or more of the sensors 202, 204, 206 into the medical scene model coordinate system. The medical scene model may then be updated at least in part on the determined coordinate transformation. For example, the medical scene model 200' may be updated to include a representation of an object 208', 210', 212' at a position in the medical scene model 200' determined based on the sensor data stream from a sensor and the coordinate transformation transforming the coordinate system for the sensor to the medical scene model coordinate system x, y, z. Determining the coordinate transformation may allow for the combining of multiple sensor data streams in one medical scene model 200', which may increase the accuracy and reliability of the medical scene model 200', and also provide for redundancy that may be useful in case of failure of one of the sensor data streams.

The coordinate transformation for each sensor may be known, or may be determined.

For example, the position and orientation of a fixed sensor 204, 202 may be known. For example, the depth information from an RGBD camera sensor 202, 204 may be defined along a viewing axis of the camera. From the known position and viewing axis of the camera in the medical scene 200, the transformation (e.g., rotation of the viewing axis and translation of the depth origin) that brings the depth information into the medical scene model coordinate system x, y, z may be determined.

In some examples, the medical scene coordinate system x, y, z may be determined to be the coincident with (e.g., the same as) the coordinate system of one or more of the sensors 202, 204. For example, if the medical scene coordinate system x, y, z is determined to be the same as the coordinate system of a first imaging sensor 202, 204, then the transformation that brings the coordinate system of a second imaging sensor 202, 204 into the coordinate system of the first sensor 202, 204, may be applied to the position information from the second imaging sensor.

As another example, the coordinate transformation for one or more sensors 202 204 may be determined by calibration (e.g., by automatic or semi-automatic calibration). For example, there may be an overlap in the field of view of two or more imaging sensors 202, 204. Depth images from two or more sensor data streams of two or more sensors 202, 204 may then be analyzed to recognize features or points that are common to both streams of depth image. The transformation that best brings the common features into alignment may then be determined as the coordinate transformation that brings a coordinate system of a first sensor into the coordinate system of a second sensor (and from there into the medical scene model coordinate system x, y, z). The common feature or features may include objects 208, 210, 212 of the medical scene 200, and/or may include a calibration object having printed thereon a known calibration pattern.

The calibration may be performed, for example, each time an existing fixed sensor 202, 204 is moved (e.g., unintentionally moved) or may be performed when a sensor 202, 204 is used for the first time. An unintentional move of one or the fixed sensors 202, 204 may be detected, and re-calibration may be initiated.

As another example, the sensor data stream may include position information from a moveable sensor 212 that monitors a position of the moveable sensor 212 relative to one or more fixed points in the medical scene 200. A calibration of this relative position may be performed to bring the position information from the moveable sensor 212 into the medical scene coordinate system x, y, z.

In some examples, the method may include analyzing the one or more sensor data streams to determine positions of one or more objects 208, 210, 212 of the medical scene 200 in the medical scene model coordinate system x, y, z. The dynamically updating the medical scene model in act 104 may then be based at least in part on the determined positions.

For example, one or more sensor data streams may include depth images of the medical scene 200. These images may be analyzed to determine that the image contains one or more objects 208, 210, 212. The positions of the one or more objects in the medical scene coordinate system x, y, z may then be determined based on the depth information and based on the coordinate transformation for the respective sensor 202, 204 into the medical scene model coordinate system.

As another example, one or more sensor data streams may include information on the configuration of an object 210, 212, such as the configuration of a controllable scanner or therapy device 210 (e.g., including a robotic arm (not shown) having joints (not shown) connecting arm components (not shown)). The configuration information may be used to determine the position of components of the scanner or therapy device 210 in the medical scene coordinate system.

As the positions of one or more objects 208, 210, 212 of the medical scene 200 changes, or as new objects enter or leave the medical scene 200, the medical scene model 200' may be updated to change the positions of the object representations 208', 210', 212' in the medical scene model 200', or to add or remove new object representations to the medical scene model 200'.

In some examples, the method may include analyzing the one or more sensor data streams to recognize one or more objects 208, 210, 212 of the medical scene 200. For example, feature recognition (e.g., based on machine learning) may be performed on depth images so as to recognize (e.g., categorize) an object of the image. For example, a depth image may include an image of a person 208, which may be recognized as such. The method may then include determining, based on the analyzing, a representation for the one or more recognized objects. For example, if it is determined that an object 208 of an image is a person, a representation 208' having the form of a person may be chosen. The dynamically updating the medical scene model 200' may then include including the determined representation 208' into the medical scene model 200'. For example, the representation 208' may be included into the medical scene model 200' at corresponding position of the object 208' in the medical scene model coordinate system x, y, z. Recognizing an object 208, 210, 212 and using a representation 208', 210', 212' of that object in the medical scene model 200 (e.g., as compared to using data directly from the sensor data streams for the representations) may allow for scene completion of the medical scene model, and hence for a more complete medical scene model. Recognizing objects 208, 210, 212 may also allow for tracking and control of specific objects.

In some examples, the determining the representation 208', 210', 212' for the one or more recognized objects 208, 210, 212 includes determining one or more geometric models 208', 210', 212' representing the geometry of the one or more recognized objects 208, 210, 212. For example, the geometric models may include point clouds, meshes (e.g., triangular meshes), parametric shape models, skeleton models, occupancy maps, or any combination thereof. The medical scene model 200' may be a combination of multiple geometrically consistent sub-models. Using geometric models to represent one or more of the objects 208, 210, 212 may allow the medical scene model 200' to include objects having a closed volume, even though one or more of the sensor data streams may not include information on the form of the whole object 208. Having object representations with a closed volume may allow, for example, for more reliable control of one or more controllable objects 210, 212 of the medical scene 200 (e.g., for collision prevention).

In some examples, a representation 208', 210', 212' for an object in the medical scene model 200' may be determined based on recognizing a portion of the object. For example, it may be determined that a depth image includes a portion of an object, and the object may be recognized based on the portion of the object. The representation determined for the recognized object may nevertheless be a representation of the whole object. For example, machine learning may be used to determine that a depth image includes the left side of a patient (e.g., a person), and it may therefore be determined that the object 208 is a person. The representation 208' for the object 208 may therefore be determined as a representation of a person 208' (e.g., including both left and right sides of a person). For example, the representation 208' may be a model of a patient, and may, for example, include an outline of a patient. For example, the representation may be a parametric shape model including a mesh having general features of a person. Parameters of the shape model may then be adjusted to fit the left side of the person, thereby to estimate in the medical scene model 200' the position and configuration of the person 208. The medical scene model 200' may therefore accurately model the medical scene 200, despite only partial information of the medical scene being supplied by the sensor data streams.

The medical scene model 200' represents the current state of the medical scene 200' based on the sensor information. The medical scene model 200' is dynamically updated based on the one or more sensor data streams. For example, the positions of one or more of the object representation 208', 210', 212' of the medical scene model 200' may be dynamically updated (e.g., progressively updated in substantially real time) based on information from the sensor data streams.

In act 106, the method includes deriving, based on the medical scene model 200', one or more medical scene model characteristics for use by one or more software applications.

The one or more medical scene model characteristics each include information characterizing the medical scene model 200'. For example, this information may include a position of one or more of the object representations 208', 212', 210' in the medical scene coordinate system x, y, z, or a relative position of one or more of the object representations 208', 212', 210' relative to another one of the object representations 208', 212', 210' in the coordinate system x, y, z. Any other characteristic of the medical scene model 200 may be determined.

Software applications that may use the medical scene model characteristics (described in more detail below) may be, for example, software applications for controlling medical imaging, for controlling moving medical equipment, for fusing medical imaging data, for detecting and preventing collisions, and/or for analyzing and optimizing clinical workflows.

Deriving characteristics for use by software applications from the medical scene model 200' rather than directly from the one or more sensors 202, 204, 206 may allow for operation of the software applications (e.g., controlling medical equipment) that is more robust to sensor failure. This may be particularly useful in medical environments where stability, continuity, and reliability may be important. For example, since the medical scene model 200' is dynamically updated based on the one or more sensor data streams, then the medical scene model 200' may persist even if one or more of the sensor data streams fails (e.g., momentarily). In an example where there is a plurality of sensors, since the characteristics are derived from the medical scene model 200' rather than directly from any particular one of the sensor data stream, then the failure of any one of the plurality of sensors 202, 204, 206 will not prevent the medical scene model 200' from being dynamically updated, and hence the characteristics used by the software applications from being derived. Further, since the medical scene model 200' does not rely on any particular one of the sensor data streams, then sensors 202, 204, 206 may be dynamically added or removed without interrupting the medical scene model 200'. For example, the method may include dynamically adding one or more sensor data streams to and/or dynamically removing one or more sensor data streams from the one or more sensor data streams that are received without interrupting the medical scene model 200'.

Stability and reliability of the derivation of medical scene model characteristics, and hence use of the software applications using these characteristics, may therefore be provided.

Deriving the medical scene model characteristics based on a medical scene model 200' that is dynamically updated based on one or more sensor data streams provides that medical scene model characteristics that best reflect a current state (e.g., substantially up-to-date state or real-time state) of the medical scene 200' may be used by the software applications. This may be important, for example, to help prevent collisions, for example, between controlled medical equipment 210 and persons 208 in the medical scene 200 and/or, for example, to allow for an accurate medical scanning to be controlled and hence achieved.

In some examples, the method includes determining, based on the one or more data streams and/or based on the medical scene model 200', one or more accuracy parameters for the one or more medical scene model characteristics. Each accuracy parameter may relate to an estimate of the accuracy of the respective medical scene model characteristic. For example, each accuracy parameter may be calculated based on an estimate of the accuracy of the corresponding characteristic, and may be, for example, a value indicating the accuracy of the corresponding characteristic. For example, each accuracy parameter may take the form of a standard error associated with the corresponding characteristic. For example, the one or more sensors 202, 204, 206 may have a known inherent or systematic error associated with the position information the one or more sensors 202, 204, 206 provide. An accuracy of the positional information of the medical scene model 200' may be estimated based on this error, and accordingly, an accuracy parameter for the one or more scene model characteristics may be determined. As another example, an error or accuracy associated with the geometric models used for the object representations 208', 210', 212' may be estimated and incorporated into the medical scene model 200'. In some examples, different parts of the scene model 200' may be assigned an accuracy parameter or confidence measure that is derived from the accuracy of the sensor inputs and/or the processing steps. The accuracy parameter may be determined for individual object representation 208', 210', 212', a group of object representations 208', 210', 212', or the complete medical scene model 200'. An accuracy parameter or confidence measure may therefore be provided for each element of the scene.

The method may include streaming the one or more medical scene model characteristics to an interface for use by the one or more software applications. Streaming medical scene model characteristics to an interface allows multiple applications to use the medical scene model data (e.g., independently) at the same time and for different purposes. As a result, a multitude of software applications may access and use the medical scene model characteristics for a multitude of different purposes, some examples of which are described in detail below. As a result, the addition and/or removal of one software application may not affect the functioning of another software application. This may be useful for operational continuity and scalability of the use of the medical scene model 200'. Further, that a multitude of software applications may use the medical scene model characteristics from one interface may reduce the need for separate models for separate applications, and hence may improve efficiency of multi-software application use.

In some examples, the method may include analyzing the derived one or more scene model characteristics to determine one or more control signals for controlling one or more objects 210, 212 of the medical scene 200, and transmitting the one or more control signals to the one or more objects 210, 212. For example, the control signals may be for controlling the movement or navigation of medical equipment controllable to move within the scene 200 (e.g., mobile scanners 210, patient beds (not shown), equipment carts or workstations 212, and/or robots or the like). The control signals may be to control movement of controllable objects 210, 212 so as to prevent collisions of the controllable objects 210, 212 and other objects, such as other moving equipment 210, 212 and/or persons 208.

In some examples, a controllable object 210 of the medical scene 200 may be a medical imaging scanner 210. For example, the medical imaging scanner may be a computed tomography (CT) scanner, a magnetic resonance imaging (MRI) scanner, a positron emission tomography (PET) scanner, a c-arm X-Ray scanner and/or the like. The method may include determining, based on the one or more medical scene characteristics, the position of a patient 208; determining, based on the position of the patient 208, an estimate of the position of one or more portions of the patient 208; and determining, based on the determined estimate of the position of one or more portions of the patient 208, one or more control signals for controlling the medical imaging scanner. For example, the medical imaging scanner may be controlled to move a scanning head to the position of the portion of the patient so as to perform a scan of that portion of the patient. For example, the medical scene characteristics may include information on the position and pose of a representation 208' of a patient 208, for example, derived based on a parametric model of the patient 208. This may be used to provide an estimate of organ positions of the patient 208. The control signals may include signals to move or change the configuration of the scanner 210 such that a scanner head is appropriately aligned with the estimated organ position. The scanner 210 may therefore be efficiently positioned to the appropriate portion of the patient for scanning. This may provide for a more efficient scanning workflow, as it may reduce the need for a technician to correctly place the patient relative to the scanner, and may obviate position-finding pre-scans.

In some examples, the scanning may be fully automated so as to recognize a patient 208 entering the medical scene 200 and perform a scan. Although this example is described with reference to medical imaging procedures, similar control may be used in other medical procedures, such as surgical procedures.

In some examples, at least one of the one or more sensor data streams is from a sensor of one of the one or more objects to which the one or more control signals is transmitted. For example, the scanner or therapy device 210 may include a robotic arm (not shown) carrying a scanner head (not shown). The robotic arm (not shown) has joints connecting arm portions (not shown). The joints include sensors producing sensor data streams including information on the relative positions of the arm portions. These sensor data streams may be used to dynamically update the medical scene model 200'. One or more control applications may use medical scene model characteristics derived from the model in order to determine control instructions for controlling the robotic arm. This control may result in the arm portions moving with respect to one another. The change in relative position is fed back into the medical scene model 200' by the joint sensor data streams. This feedback may improve the accuracy and reliability of the medical scene model 200' and thus, improve control of moveable objects 212, 210.

In some examples, the method may include receiving medical imaging data from the medical imaging scanner 210 of the medical scene 200. The dynamically updating the medical scene model 200' may be based at least in part on the medical imaging data. For example, the medical imaging data may be a medical imaging dataset including a three-dimensional representation of a portion of a patient. For example, the medical dataset may be derived from computed tomography, magnetic resonance, positron emission tomography, single photon emission computed tomography, ultrasound, or another scan modality. The scan data may be from multiple two-dimensional scans or may be formatted from a 3D scan. The medical imaging scanner 210 may be controlled by one or more control applications to send the medical imaging data for inclusion into the medical scene model 200'. Updating the medical scene model 200' based on medical imaging data sets may allow the internal information of the patient 208 to be incorporated, for example, in addition to external information that may be visible by one or more camera sensors 204, 202. This may allow for efficient collection of data sets. For example, an ultrasound scan identifying the internal position of one or more organs of the patient 208 may be received and included into the medical scene model 200' at the appropriate position within the representation 208 of the patient. This information may then be used to control the position of a further scanner (e.g., a CT scanner) relative to the patient 208 so as to perform a further scan at an accurate location of the organ desired for imaging.

In some examples, the method may include receiving further medical imaging data from a further medical imaging scanner of the medical scene 200. The dynamically updating the medical scene model 200' may be based at least in part on the further medical imaging data. The method may further include determining a relative position of the medical imaging scanner and the further medical imaging scanner, and fusing, based on the determined relative position, the medical imaging data with the further medical imaging data. For example, a first scanner (not shown) may collect ultrasound data of a patient 208, and a second scanner 210 may collect CT data of a patient. The relative positions of the first scanner and the second scanner 210, for example, relative to the patient 208 may be derived from their representations in the medical scene model 200'. The corresponding relative positions of the ultrasound data and the CT data may therefore be determined, and hence, the different data modalities may be overlaid or fused in three-dimensional space. Fusing medical imaging data of different modalities may allow a more complete image of the patient 208, for example, for use by a surgeon. Fusing medical imaging data based on determined relative positions of the scanners from the medical scene model 200' may be more efficient and reliable than fusing data based only on the medical data sets themselves.

In some examples, non-imaging medical data such as electrocardiogram (ECG) data, blood pressure data, or ventilation data may be received and incorporated into the medical scene model 200'. Further, in some examples, other types of sensors may be used to provide further information for the medical scene model 200', such as data from an inertial measurement unit (IMU), microphones, microphone arrays, radio frequency identification (RFID) sensors, pressure sensors, and/or temperature sensors and the like.

In some examples, the method may include determining, based on the one or more medical scene characteristics, a position of a radiation source. The method may include estimating, based on the determined position of the radiation source, a radiation characteristic at one or more locations in the medical scene model. For example, the radiation characteristic may be a value indicating a radiation exposure or dose at one or more locations in the medical scene model. For example, the radiation source may be a medical scanner head (e.g., of an X-Ray scanner or a scanner based on radio frequency radiation). Based on an estimate of the position of the scanner head from a representation in the medical scene model 200', and based on a scanning power provided, an estimate of the distribution of radiation in the medical scene 200 may be calculated. This may be calculated, for example, using a finite element method (FEM) that may include subdividing the medical scene model 200' into finite elements and calculating radiation at each of the elements. A radiation dose or exposure at a particular object representation, such as a person representation 208' of the medical scene model 200', may be calculated. A warning may be provided if a predefined threshold of radiation exposure is exceeded. As another example, if such a threshold is exceeded, then a control signal may be transmitted to the radiation source to instruct the radiation source to cease producing radiation. This may allow safety of medical imaging scanning to be monitored and maintained.

In some examples, the method may include receiving information from a software application, and determining, based on the received information, a detail level for the medical scene model. The dynamically updating the medical scene model 200' may be based at least in part on the determined detail level. For example, the level of detail of the medical scene model 200' may be dependent on one or more of the software application using the data. For example, if at a given time there is only one software application utilizing the derived medical scene characteristics, and this software application only requires medical scene characteristics including information of the approximate location of an object 208, 210, 212 in the medical scene 200, a detail level of the medical scene model 200' required to provide this information may be determined to be relatively low. In this case, for example, it may be determined that the medical scene model 200' need not include parametric geometric models for each of the objects 208, 210, 212 of the medical scene 200, and instead, the medical scene model 200' may consist only of one or more positions of simple object representations 208', 210', 212' in the medical scene model 200'. However, if a software application requires more complex medical scene model characteristics, for example, including object recognition and tracking information, then the detail level of the medical scene model 200' may need to be relatively high, and the medical scene model 200' may include more detail. For example, one or more analytics modules may be invoked, for example, for detecting and tracking persons such as patients or other medical equipment to incorporate the more detailed information into the medical scene model 200' when required. Basing the medical scene model 200' detail on the intended use of the medical scene model characteristics may provide for more flexible and efficient scene model generation that uses processing power commensurate with the intended task.

In some examples, the method includes rendering the medical scene model 200' to produce a representation of the medical scene model 200' projected on a two-dimensional plane. For example, a visualization software application may render all components (e.g., object representations 208', 212', 210') of the medical scene model 200' in real time (e.g., concurrently with the dynamic updating of the medical scene model 200'). Rendering may include, for example, collapsing the volume 214 or a portion of the volume 214 of the medical scene model 200' onto a two-dimensional viewing plane. This may allow remote observation and/or interaction with the medical scene model 200'. For example, the rendered viewing plane may be used as an input for a virtual reality (VR) headset allowing remote users to observe and control the medical scene model 200'. As another example, the rendered viewing plane may be used as an input for an augmented reality (AR) headset (e.g., worn by a person 208 in the medical scene 200). The position and pose of the person 208 in the medical scene 200 may be determined, for example, as described above, and the viewing plane for rendering determined based on the determined position and pose. The augmented reality (AR) headset may then overlay rendering of information (e.g., medical imaging or other anatomical information) from the medical scene model 200' onto the view of the medical scene 200 experienced by the person. This may allow guidance for a physician, for example, during surgery, and hence, may help improve and/or make more efficient medical workflows.

In some examples, one or more of the sensor data streams may each include a stream of data packets, and each data packet may include a time stamp provided by a sensor clock of the sensor from which the data packet is acquired. The time stamps may help improve the accuracy of the medical scene model 200', for example, if data packets arrive from one or more sensors 202, 204, 206 out of sequence, if sensors 202, 204, 206 have variable streaming rates, or if different sensors 202, 204, 206 have different streaming rates. In some examples, the method may include synchronizing one or more of the sensor clocks with a clock associated with the medical scene model. This may help provide that the medical scene model 200' is accurate with respect to the relative dynamics of different objects 206, 210, 212 for example, captured by different sensors 202, 204, 206. The synchronization of the clocks may be, for example, by network time protocol (NTP).

In some examples, the method includes determining one or more dynamic changes to the medical scene model 200' and storing the determined one or more dynamic changes. The method may include determining, based on the stored one or more dynamic changes, a trajectory of one or more object representations 208', 210', 212' of the medical scene model 200'. Determining the trajectory of an object may be useful, for example, in workflow analysis and optimization, as well as in collision prevention, for example. Storing dynamic changes may allow for trajectories of one or more objects representations 208', 210', 212' to be determined without having to store the entire medical scene model 200' at different time steps. This may be efficient. In some examples, the method may include integrating one or more medical scene model characteristics over time to determine time integrated characteristics. In some examples, the method may include monitoring medical devices and proper functioning of the medical devices under specified guidelines to determine if maintenance may be required. In some examples, the method may include monitoring technicians and medical procedures to determine information for workflow optimization analysis for efficient operation in scanning rooms and/or operating rooms, for example.

Figure 4:
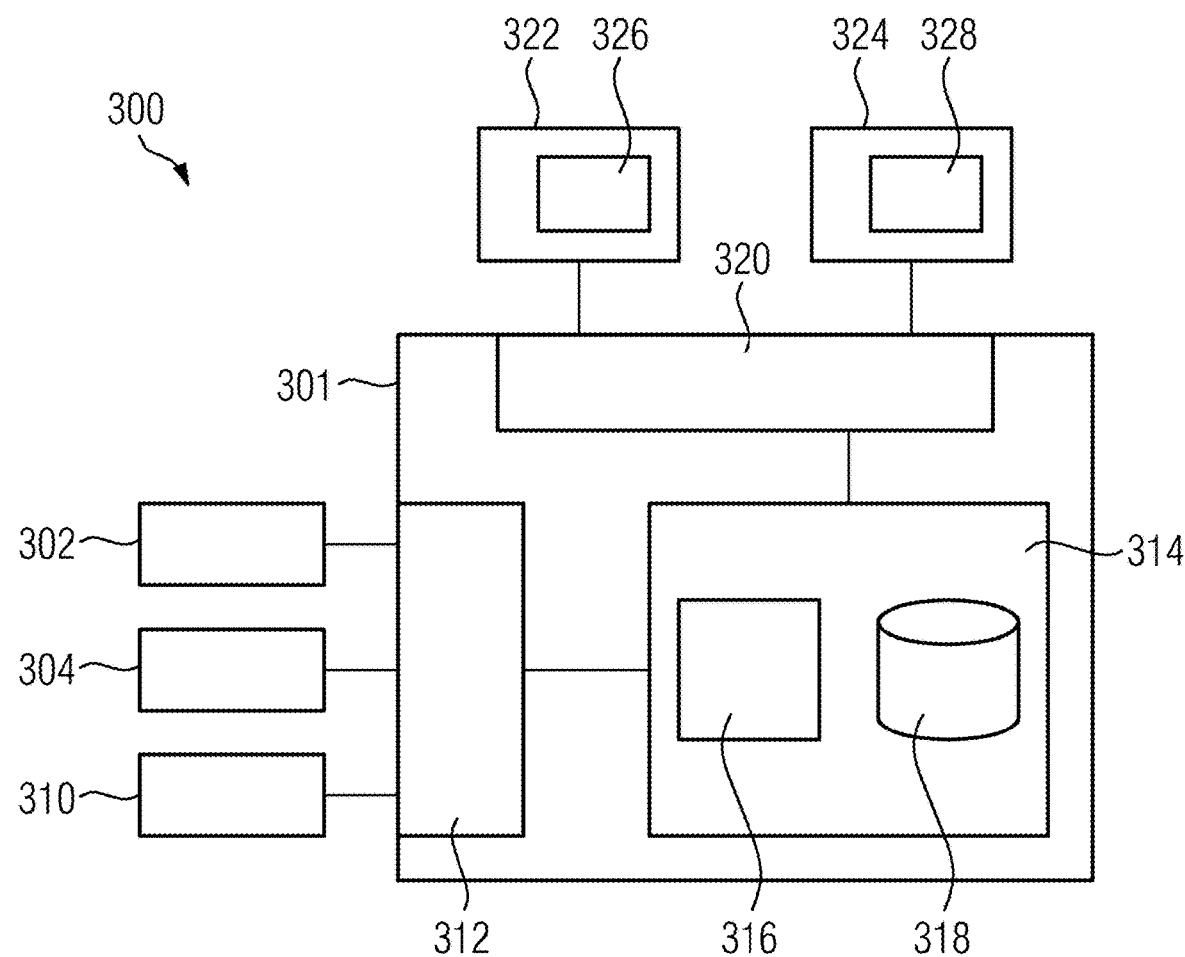
FIG. 4 illustrates schematically a system including an apparatus according to an example.

FIG. 4 illustrates schematically a system 300 including an apparatus 301 for deriving one or more medical scene model characteristics for use by one or more software applications, according to an example.

The apparatus 301 includes an acquisition unit 312, a processing system 314 including a processor 316 and a memory 318, and an interface 320. The apparatus 302 and/or the overall system 300 may be arranged to perform the method described above with reference to FIGS. 1 to 2b. The acquisition unit 312 may be configured to receive one or more sensor data streams from one or more sensors 302, 304, 310. Each sensor data stream includes position information relating to a medical scene 200. The sensors 302, 304, 310 may be the same or similar to the sensors 204, 202, 212 described above with reference to FIGS. 1 to 2b. The sensors 302, 304, 310 are each communicatively coupled to the acquisition unit 312. The sensors 302, 204, 310 may communicate with the acquisition unit 312, for example, via a wired or wireless connection (e.g., via a computer network such as the Internet) using a protocol such as, for example, TCP/IP.

The memory 318 may have instructions stored thereon. When the instructions are executed by the processor 316, the instructions cause the apparatus 301 to perform the method described above with reference to FIGS. 1 to 2b. For example, the processor 316 may dynamically update a medical scene model 200' including a three-dimensional representation 214 of a state of a medical scene 200 based on one or more sensor data streams received by the acquisition unit 312, and may derive, based on the medical scene model 200', one or more medical scene model characteristics for use by one or more software applications 326, 328, as described above. In some examples, the one or more software applications may be run on the processor 316. However, in other examples, the derived medical scene model characteristics are streamed to the interface 320 for use by one or more software applications 326, 328 that may, for example, be running on one or more further processing systems 322, 324, respectively. The software applications 326, 328 may each extract medical scene model characteristics from the interface 320, for example, for use in monitoring and/or controlling one or more objects 208, 212, 210 of the medical scene 200. The further processing systems 322, 324 may be communicatively coupled to the interface 320 via a wired or wireless connection (e.g., via a computer network such as the Internet) using a protocol such as, for example, TCP/IP.

Figure 5:
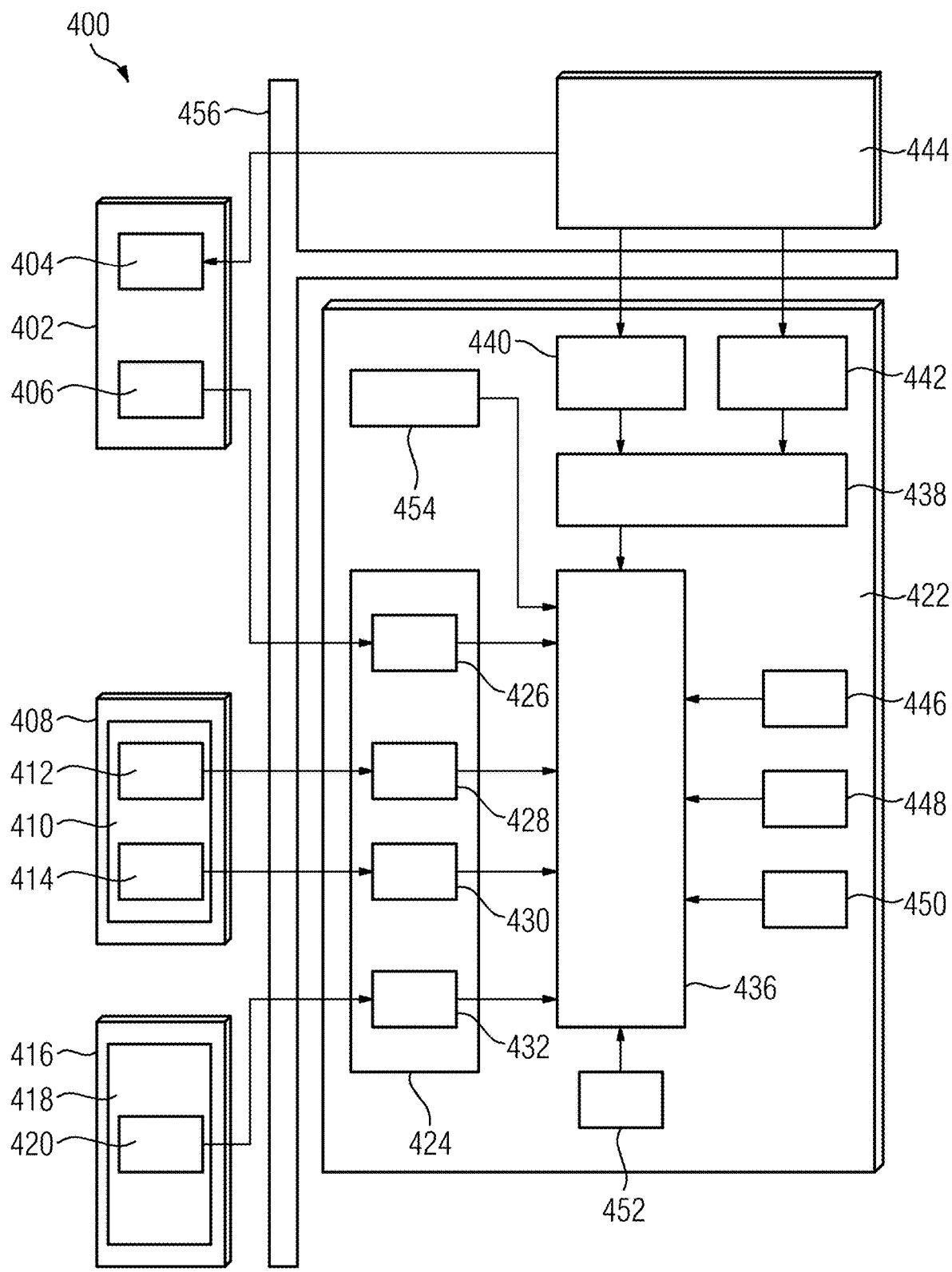
FIG. 5 illustrates schematically a system including an apparatus according to an example.

FIG. 5 illustrates schematically a system architecture 400 including devices 402, 408, 416, 422, 444 in communication with one another via a communication network 456 utilizing TCP/IP, according to an example. The devices are a scanner or therapy device 402, a first sensor computer 408, a second sensor computer 416, a server 422, and an application computer 444. Each device runs one or more software application modules, which may run on a processing system (not shown) including a processor and a memory (not shown) of each respective device 402, 408, 416, 422, 444. The server 422, like the apparatus of 301 of FIG. 4, may be an apparatus configured to perform the method described above with reference to FIGS. 1 to 2b.

Referring to FIG. 5, the scanner or therapy device 402, which may be an object of a medical scene 200, includes a scan control module 402 and a sensor client module 406. For example, as described above, the medical imaging scanner or therapy device 402 may include sensors that detect a position and/or configuration of the scanner or therapy device 402, and the sensor client module 406 may be accordingly arranged to provide a data stream including information on the position and/or configuration of the scanner. The scan control module 404 may receive control signals to enable the position and/or configuration of the scanner 402 to be controlled.

The first sensor computer 408 includes a sensor client module 410 including a first sub-module 412 for providing a sensor data stream from a first RGBD sensor viewing the medical scene 200, and a second sub-module 412 for providing a sensor data stream from a second RGBD sensor viewing the medical scene.

The second sensor computer 416 includes a sensor client module 418 including a sub-module 420 for providing a sensor data stream from a third RGBD sensor viewing the medical scene 200.

The server 422 includes an acquisition module 424 including a first sensor acquisition sub-module 426 for acquiring the sensor data stream from the sensor client module 406 of the scanner or therapy device 402, a second sensor acquisition sub-module 428 for acquiring the sensor data stream from the first sub-module 412 of the first sensor computer 408, a third sensor acquisition sub-module 430 for acquiring the sensor data stream from the second sub-module 414 of the first sensor computer 408, and a fourth sensor acquisition sub-module 432 for acquiring the sensor data stream from the sub-module 420 of the second sensor computer 416. The data may be received by the sub-modules 426, 428, 430, 432, for example, over the computer network 456. Each of the sensor acquisition sub modules 426, 428, 430, 432 is for providing (e.g., advertising) respective sensor data streams to a scene model module 436 of the server 422. The scene model module 436 dynamically updates a scene model 200' of the medical scene 200 based on the sensor data streams.

The server 422 includes a calibration publisher module 454 for providing (e.g., advertising) calibration information to the scene model module 436 so that each of the data streams may be appropriately calibrated with respect to one another when updating the medical scene model 200', for example, as described above.

The server 422 includes a renderer 452 for rendering the scene model 200' or components thereof, for example, as described above (e.g., for visualization of the medical scene model 200' of the scene model module 436).

The server 422 includes a point cloud engine 466 for determining a point cloud representing the medical scene 200 based on one or more of the RGBD sensor data. For example, the point cloud engine 446 may acquire (e.g., subscribe) RGBD sensor information from the scene model module 436. The point cloud engine 446 may then transform the RGBD sensor information, which may include, for example, a depth map, into a point cloud representing the medical scene 200. The point cloud engine may then provide (e.g., advertise) the point cloud to the scene model module 436, which may then incorporate the point cloud into the medical scene model 200'.

The server 422 includes a person detecting engine 448 for detecting a person of the medical scene 200 based on the point cloud data. For example, the person detecting engine 448 may acquire (e.g., subscribe) point cloud data from the scene model module 436. The person detecting engine 448 may then analyze the point cloud so as to recognize (e.g., based on machine learning) that the point cloud includes a person. The person detecting engine may then generate a bounding box bounding the volume in which a person has been detected. The person detecting engine 448 may then provide (e.g., advertise) the bounding box to the scene model 436, which may then incorporate the bounding box into the medical scene model 200'. Providing a bounding box may be useful, for example, for collision prevention, without requiring a full modeling of patient pose or geometry.

The server 422 includes a patient modeling engine 450 for recognizing and determining a geometric model for a person of the medical scene 200, based on one or more of the RGBD sensor data or point cloud data. For example, patient modeling engine 450 may acquire (e.g., subscribe) RGBD sensor information or, for example, point cloud data from the scene model module 436. The patient modeling engine 450 may analyze the data so as to recognize (e.g., based on machine learning) that the sensor information or point cloud includes a person. The patient modeling engine 450 may then generate a model of the person (e.g., a parametric shape model of the person including an estimate of the pose of the person) or another avatar such as a skeleton model. The patient modeling engine 450 may then provide (e.g., advertise) the person model or other avatar to the scene model module 436, which may then incorporate the person model or other avatar into the medical scene model 200'. Providing a person model may be useful, for example, where the precise position of a portion of a patient is important (e.g., when controlling a medical imaging scanner to scan a particular portion of a person is desired).

The point cloud engine 446, the person detector engine 448, and/or the patient modeling engine 450 may be invoked by the scene model module 436, as required (e.g., as required to provide an appropriate detail level of the medical scene model based on the needs or request of one or more software application using the medical scene model characteristics derived by the scene model module 436). This may provide for efficient utilization of the engines 446, 448, 450 and hence for efficient utilization of the processing resources of the server 422.

The server 422 includes an application interface 438 between the scene model module 438 and first 440 and second 442 application sever modules of the server 422. The scene model module 438 may provide (e.g., stream) medical scene model characteristics to the interface 438. The first application server module 440 may extract one or more medical scene model characteristics from the interface 438 as required by a first application of the application computer 444 with which the first application server module 440 communicates. The first application server module 440 may then provide (e.g., transmit over network 456) the extracted medical scene model characteristics to the application computer 444, which then may be used by the first application running on the application computer 444. Similarly, the second application server module 442 may extract one or more (e.g., different) medical scene model characteristics from the interface 438, as required by a second application of the application computer 444 with which the second application server module 442 communicates. The second application server module 440 may then provide (e.g., transmit over network 456) the extracted medical scene model characteristics to the application computer 444, which may then be used by the first application running on the application computer 444.

The application computer 444 may run the first and second software applications for controlling a scanner controlled by the scanner computer. For example, the medical scene model characteristics acquired by the first and second applications of the application computer may relate to the position of a representation of the scanner 402 relative to the position a particular portion of a model representation of a detected person, in the medical scene model 200'. The first and second applications of the application computer 444 may use this information to determine one or more control signals for controlling a scanning head of the scanner 402 to move to be appropriately positioned adjacent to the portion of the person (e.g., so that a scan of the portion of the person may begin). The application computer 44 may provide (e.g., transmit over computer network 456), the control signal to the scan control module 404 of the scanner 402. The scanner 402 may therefore be controlled to move accordingly.

The above examples may provide for more efficient medical workflows, for example, for more efficient medical imaging. The scene model module 436 deriving characteristics based on the medical scene model 200', rather than directly from the sensors, may allow for control that is more robust to sensor failure, and hence may allow for stability, continuity and reliability of the control. The scene model module 436 deriving the medical scene model characteristics based on a medical scene model 200' that is dynamically updated based on sensor data streams may help provide that medical scene model characteristics used for control are up-to-date, and hence may provide for more accurate control. The scene model module 436 streaming the medical scene model characteristics to the application interface 438 allows multiple application modules to use the medical scene model data (e.g., independently) at the same time and/or for different purposes. This may provide, for example, for efficient and consistent control of different pieces of controllable medical equipment.

The above examples are to be understood as illustrative examples of the invention. Any feature described in relation to any one example may be used alone or in combination with other features described and may also be used in combination with one or more features of any other of the examples, or any combination of any other of the examples. Equivalents and modifications not described above may also be employed without departing from the scope of the invention, which is defined in the accompanying claims.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of deriving one or more medical scene model characteristics for use by one or more software applications, the method comprising:
   receiving one or more sensor data streams, each sensor data stream of the one or more sensor data streams comprising position information relating to a medical scene;
   dynamically adding at least one sensor data stream to the one or more sensor data streams that are received, dynamically removing at least one sensor data stream from the one or more sensor data streams that are received, or dynamically adding at least one sensor data stream to the one or more sensor data streams that are received and dynamically removing at least one sensor data stream from the one or more sensor data streams that are received;
   dynamically updating, based on the dynamically adding, the dynamically removing, or the dynamically adding and the dynamically removing of the at least one sensor data stream, a medical scene model, the medical scene model comprising a three-dimensional (3D) representation of a state of the medical scene; and
   deriving, based on the medical scene model, the one or more medical scene model characteristics.

2. The method of claim 1, wherein at least one sensor data stream of the one or more sensor data streams comprises information relating to an image of the medical scene.

3. The method of claim 1, wherein at least one sensor data stream of the one or more sensor data streams comprises depth information relating to a depth, from a sensor, of one or more objects of the medical scene.

4. The method of claim 1, wherein the one or more sensor data streams are received from a respective plurality of sensors,
   wherein the method further comprises determining a coordinate transformation for transforming a coordinate system for at least one sensor of the one or more sensors into a medical scene model coordinate system, and
   wherein the dynamically updating the medical scene model is based at least in part on the determined coordinate transformation.

5. The method of claim 1, further comprising determining positions of one or more objects of the medical scene in a medical scene model coordinate system, the determining of the positions of the one or more objects of the medical scene comprising analyzing the one or more sensor data streams,
   wherein the dynamically updating the medical scene model is based at least in part on the determined positions.

6. The method of claim 1, further comprising:
   recognizing one or more objects of the medical scene, the recognizing comprising analyzing the one or more sensor data streams; and
   determining, based on the analyzing, a representation for the one or more recognized objects,
   wherein the dynamically updating the medical scene model comprises including the determined representation into the medical scene model.

7. The method of claim 6, wherein the determining the representation for the one or more recognized objects comprises determining one or more geometric models representing a geometry of the one or more recognized objects.

8. The method of claim 6, where at least one object of the one or more objects of the medical scene is a patient, and the determined representation comprises a model of the patient.

9. The method of claim 1, further comprising receiving medical imaging data of the medical scene from a medical imaging scanner,
   wherein the dynamically updating the medical scene model is based at least in part on the medical imaging data.

10. The method of claim 1, further comprising streaming the one or more medical scene model characteristics to an interface for use by the one or more software applications.

11. The method of claim 1, further comprising:
   determining one or more control signals for controlling one or more objects of the medical scene, the determining of the one or more control signals comprising analyzing the one or more scene model characteristics; and
   transmitting the one or more control signals to the one or more objects.

12. The method of claim 11, wherein at least one sensor data stream of the one or more sensor data streams is from a sensor of an object of the one or more objects to which the one or more control signals is transmitted.

13. The method of claim 1, further comprising:
receiving information from a software application of the one or more software applications; and
determining, based on the received information, a detail level for the medical scene model,
wherein the dynamically updating the medical scene model is based at least in part on the determined detail level.

14. The method of claim 1, further comprising producing a representation of the medical scene model projected on a two-dimensional plane, the producing of the representation of the medical scene model comprising rendering the medical scene model.

15. The method of claim 1, wherein the one or more sensor data streams comprises at least two sensor data streams.

16. An apparatus for deriving one or more medical scene model characteristics for use by one or more software applications, the apparatus comprising:
a processor configured to:
receive one or more sensor data streams, each sensor data stream of the one or more sensor data streams comprising position information relating to a medical scene;
dynamically add at least one sensor data stream to the one or more sensor data streams that are received, dynamically remove at least one sensor data stream from the one or more sensor data streams that are received, or dynamically add at least one sensor data stream to the one or more sensor data streams that are received and dynamically remove at least one sensor data stream from the one or more sensor data streams that are received;
receive position parameters from a medical imaging scanner, the position parameters describing a position, an orientation, or the position and the orientation of the medical imaging scanner;
dynamically update, based on the one or more sensor data streams and the position parameters, imaging parameters, or the position parameters and the imaging parameters, a medical scene model, the medical scene model comprising a three-dimensional (3D) representation of a state of the medical scene; and
derive, based on the medical scene model, the one or more medical scene model characteristics.

17. The apparatus of claim 16, wherein the one or more sensor data streams comprises at least two sensor data streams.

18. In a non-transitory computer-readable storage medium that stores instructions executable by one or more processors to derive one or more medical scene model characteristics for use by one or more software applications, the instructions comprising:
receiving one or more sensor data streams, each sensor data stream of the one or more sensor data streams comprising position information relating to a medical scene;
dynamically adding at least one sensor data stream to the one or more sensor data streams that are received, dynamically removing at least one sensor data stream from the one or more sensor data streams that are received, or dynamically adding at least one sensor data stream to the one or more sensor data streams that are received and dynamically removing at least one sensor data stream from the one or more sensor data streams that are received;
dynamically updating, based on the one or more sensor data streams, a medical scene model, the medical scene model comprising a three-dimensional (3D) representation of a state of the medical scene;
deriving, based on the medical scene model, the one or more medical scene model characteristics,
determining, based on the one or more medical scene model characteristics, a position of a patient;
determining, based on the position of the patient, an estimate of a position of one or more portions of the patient; and
determining, based on the estimate of the position of the one or more portions of the patient, one or more control signals for controlling a medical imaging scanner.

19. The non-transitory computer-readable storage medium of claim 18, wherein the one or more sensor data streams comprises at least two sensor data streams.

* * * * *